United States Patent [19]

Nakamura et al.

[11] 4,107,300

[45] Aug. 15, 1978

[54] STABLE SOLID AGRICULTURAL CHEMICAL COMPOSITION AND PROCESS FOR PREPARATION THEREOF

[75] Inventors: Toshiie Nakamura, Kusatsu; Hiromichi Shimizu; Kyuichi Tanaka, both of Shiga; Akihiko Kunitomo; Kinji Tanizawa, both of Moriyama, all of Japan

[73] Assignee: Sankyo Company Limited, Tokyo, Japan

[21] Appl. No.: 508,354

[22] Filed: Sep. 23, 1974

[30] Foreign Application Priority Data

Sep. 28, 1973 [JP] Japan ............................ 48-109024

[51] Int. Cl.$^2$ ............................................. A01N 9/36
[52] U.S. Cl. .................................... 424/200; 424/154; 424/211; 424/216; 424/246; 424/268; 424/273 R; 424/286; 424/335

[58] Field of Search ............... 424/273, 286, 289, 211, 424/217, 200, 335, 246, 268, 154

[56] References Cited

U.S. PATENT DOCUMENTS

| | | | |
|---|---|---|---|
| 3,541,213 | 11/1970 | Klopping | 424/273 |
| 3,657,443 | 4/1972 | Klopping | 424/273 |

*Primary Examiner*—V. D. Turner
*Attorney, Agent, or Firm*—Toren, McGeady and Stanger

[57] ABSTRACT

In a solid agricultural chemical composition containing an unstable active ingredient, when a small amount of anhydrous calcium chloride, calcium chloride monohydrate or calcium chloride dihydrate is incorporated, the active ingredient can be highly stabilized. The quality and physical properties, such as flowability, of the solid agricultural chemical composition are not at all degraded by incorporation of said stabilizer.

4 Claims, No Drawings

STABLE SOLID AGRICULTURAL CHEMICAL COMPOSITION AND PROCESS FOR PREPARATION THEREOF

This invention relates to a stable agricultural chemical composition and a process for the preparation thereof. More particularly, the invention relates to a stable solid agricultural chemical composition comprising an unstable agricultural chemical active ingredient and, incorporated therein, at least one calcium chloride stabilizer selected from anhydrous calcium chloride calcium chloride monohydrate and calcium chloride dihydrate.

Recently, environmental pollution by agricultural chemicals has a social problem, and use of stable agricultural chemical active ingredients such as DDT, BHC and cyclodiene insecticides is now controlled and unstable agricultural chemical active ingredients having less accumulative property and hardly causing environmental pullution are extensively used instead.

In such state of the art, development of a technique of keeping an easily-decomposing active ingredient stable in an agricultural chemical preparation is of great significance.

If such unstable active ingredient decomposes in an agricultural chemical preparation, not only the biological effect is reduced but also physical properties of the preparation are drastically degraded to reduce the commercial value. Further, decomposition of the active ingredient often results in promotion of phytotoxicity to cultivation plants.

This tendency is especially conspicuous when an unstable agricultural chemical active ingredient is mixed with a mineral substance as a carrier and formed into a solid agricultural chemical preparation such as powder, wettable powder, seed dressing powder, coarse powder, fine granule or granule.

By the term "unstable agricultural chemical active ingredient" referred to in the instant specification are meant, for example, fungicides such as 3,3'-ethylenebis(-tetrahydro-4,6-dimethyl-2H-1,3,5-thiadiazine-2-thione) (Thiadiazine), dithiocarbamate agents such as zinc ethylenebisdithiocarbamate (Zineb) and manganese ethylenebisdithiocarbamate (Maneb), and methyl 1-(butylcarbamoyl)-2-benzimidazole carbamate (Benomyl), organic phosphorus insecticides such as O,O-dimethyl-S-(N-methyl-N-formylcarbamolymethyl) phosphorodithioate (Formothion), O,O-dimethyl-S-2-(ethylthio)ethyl phosphorodithioate (Thiometon) and O,O-dimethyl-O-(5-phenyl-3-isoxazolyl) phosphorothioate (Dimex), acaricides such as 2-(p-tert-butylphenoxy)-isopropyl-2'-chloroethylsulfite (Aramite) and 2-(p-tert-butylphenoxy)-1-ethyl-O-tolylsulfite (C-940) and antibiotics such as cycloheximide (Actidione). However, it must be noted that unstable agricultural chemical active ingredients to be used in this invention are not limited to those mentioned above.

A solid agricultural chemical preparation including any of the foregoing active ingredients is very unstable under elevated temperature and high humidity conditions, and in high temperature and high humidity countries such as Japan, a special preparation-forming technique is required in order to keep preparations stable for a long time under such climate conditions.

Various research works have heretofore been made for obtaining stable solid agricultural chemical preparations of easily-decomposing active ingredients such as mentioned above, and use of a specific inert carrier or adjuvant or use of a specific inactivating agent or stabilizing agent has been proposed. However, these conventional proposals are not generally applicable to all of unstable active ingredients inclusively but troublesome examinations are required with respect to individual active ingredients respectively.

As a result of research works made with a view to providing a stable solid agricultural chemical composition comprising an unstable active ingredient in the much stabilized state, we have found that when a small amount of at least one member selected from anhydrous calcium chloride, calcium chloride monohydrate and calcium chloride dihydrate (hereinafter referred to as "calcium chloride stabilizer" inclusively) is incorporated in solid agricultural chemical preparation containing an unstable active ingredient, a stable solid agricultural chemical preparation can be obtained and the stabilizing effect of the calcium chloride stabilizer is very excellent regardless of the kind of the unstable active ingredient. Based on this finding, we have now completed this invention.

More specifically, in accordance with this invention, there is provided a stable solid agricultural chemical composition comprising an unstable agricultural chemical active ingredient and incorporated therein, at least one of calcium chloride stabilizers selected from the group consisting of anhydrous calcium chloride, calcium chloride monohydrate and calcium chloride dihydrate.

Calcium chloride has a high hygroscopic property, and it absorbs moisture in air and it readily deliquesces. Because of this property, it has been apprehended that when the calcium chloride stabilizer is incorporated into a solid agricultural chemical preparation, bad influences would be imposed on the stability of the active ingredient and the physical properties of the agricultural chemical preparation. Therefore, it is unknown in the art that calcium chloride has been incorporated in an agricultural chemical preparation for stabilization.

In view of the foregoing, it is quite surprising that when a small amount of the calcium chloride stabilizer is incorporated into a solid agricultural chemical preparation containing an unstable active ingredient, even under severe high temperature and high humidity conditions, the unstable active ingredient in the preparation under a proper packing can be highly stabilized and the physical properties of the preparation, especially the flowability which is important for a preparation to be sprayed, are hardly degraded by incorporation of the calcium chloride stabilizer.

Incidentally, a drying agent which is more effective in reducing the equilibrium water content in air, such as silica gel, alumina or anhydrous sodium sulfate, is inferior in the effect of preventing degradation of the quality and even when such drying agent is incorporated for stabilization of an unstable agricultural chemical active ingredient, no satisfactory results can be obtained. Even though plaster is effective to some extent, it has been confirmed that if a solid agricultural chemical preparation into which plaster has been incorporated is stored for a long time under a high humidity condition, there is brought about a defect that the flowability of the powdery or granular preparation is degraded.

In contrast, the calcium chloride stabilizer of this invention, even if incorporated in a small amount, exhibits a prominent degradation-preventing effect such as mentioned above and it is further characterized in that no danger is involved in handling, it is readily available at a low cost and no risk of promotion of the phytotoxicity on applied cultivation plants is brought about. In short, this invention provides a very effective and practical means for maintaining stability of the quality in various solid agricultural chemical preparations.

In the solid agricultural chemical composition of this invention, the calcium chloride stabilizer is generally incorporated in an amount of 0.1 to 20% by weight based on the finished preparation, though the amount of the stabilizer incorporated may vary depending on the kind of the active ingredient. It is preferred that the amount of the calcium chloride incorporated be 3 to 10% by weight based on the finished preparation. It must be noted, however, that the amount of the calcium chloride incorporated is not limited to those included in the above-mentioned range.

The calcium chloride stabilizer can be incorporated into the solid agricultural composition by various methods. For instance, the powdery or granular stabilizer is incorporated into the raw material and the mixture is finely pulverized to form powder, wettable powder, seed dressing powder or the like. Furthermore, the calcium chloride stabilizer having a finely divided form or having the particle size adjusted within a desired range is added to powder, wettable powder, seed dressing powder, coarse powder, fine granule or granule which has been prepared in advance, and the mixture is agitated to disperse the stabilizer uniformly in such solid preparation. These solid agricultural chemical preparations can be prepared according to customary methods by using inert solid carriers, surface active agents and other adjuvants employed customarily in the field of agricultural chemicals.

In order to prolong the stabilizing effect and store the stabilized agricultural composition of this invention under stable conditions for a very long time, it is preferred that the stabilized agricultural chemical composition be packaged with a packaging material having a high moisture resistance such as an aluminum foil-bonded cellophane bag (aluminum foil bag), an aluminum-laminated kraft bag, a plastic vessel and a glass bottle.

The stable agricultural chemical composition of this invention and the process for the preparation thereof will now be described in more detail by reference to the following Examples.

EXAMPLE 1 (POWDER)

A ribbon-type mixer is charged with 6 parts of Thiadiazine, 3 parts of anhydrous calcium chloride, 2 parts of white carbon and 89 parts of clay, and the mixture is blended and pulverized by a hammer mill to obtain a powder.

EXAMPLE 2 (POWDER)

A ribbon-type mixer is charged with 88 parts of clay and 4 parts of white carbon, and while the mixture is being blended under agitation, 3 parts of Dimex is added and allowed to be absorbed in the mixture completely. The mixture is pulverized by a hammer mill, and the pulverized product is charged in the ribbon-type mixer again and 5 parts of powdery anhydrous calcium chloride is added thereto. The mixture is sufficiently blended under agitation to obtain a powder.

EXAMPLE 3 (WETTABLE POWDER)

A ribbon-type mixer is charged with 80 parts of thiadiazine, 3 parts of Rapisol BB-75 L (anionic surface active agent of the succinate type manufactured by Nippon Yushi K. K., Japan), 5 parts of powdery sodium lignin-sulfonate, 3 parts of anhydrous calcium chloride and 9 parts of white carbon, and the mixture is blended and then pulverized by a hammer mill to obtain a wettable powder.

EXAMPLE 4 (WETTABLE POWDER)

A ribbon-type mixer is charged with 35 parts of white carbon, 15 parts of basic magnesium charbonate, 5 parts of powdery sodium lignin-sulfonate and 5 parts of anhydrous calcium chloride, and while the mixture is being agitated, 40 parts of C-940 is added thereto. Mixing under agitation is continued for a while to make C-940 absorbed in the mixture completely. Then, the mixture is finely pulverized by a hammer mill to obtain a wettable powder.

EXAMPLE 5 (WETTABLE POWDER)

A ribbon-type mixer is charged with 20 parts of white carbon, 26 parts of diatomaceous earth, 5 parts of Neogen powder (powder containing 30% of sodium alkylarylsulfonate, manufactured by Daiichi Kogyo Seiyaku K. K., Japan) and 2 parts of polyvinyl alcohol, and a liquid formed in advance by mixing 40 parts of Dimex and 2 parts of Parachor WS (surface active ingredient containing both nonionic and anionic ingredients, manufactured by Nippon Nyukazai K. K., Japan) is added dropwise to the mixture under agitation to make the liquid absorbed in the mixture. The mixture is pulverized by a hammer mill, and 5 parts of powdery anhydrous calcium chloride is added to the pulverized mixture and the mixture is sufficiently blended under agitation again by the ribbon-type mixer to obtain a wettable powder.

EXAMPLE 6 (FINE GRANULE F)

A ribbon-type mixer is charged with 92 parts of silica sand, more than 90% of particles of which have a size of 0.063 mm to 0.210 mm, and 2 parts of New Coal-560 (polyoxyethylene nonylphenyl ether manufactured by Nippon Nyukazai K. K.) is added under agitation to wet the surface of the silica sand completely. Then, 5 parts of the Thiadiazine wettable powder obtained in Example 3 (containing 3% of anhydrous calcium chloride) is added to the wetted silica sand and the mixture is sufficiently blended to form a coating on the silica sand surface. In this state, because of the viscousness among granules, the flowability is inferior. Accordingly, 1 part of white carbon is added to the granules to complete the coating of the granule surface, and a fine granule F having a good flowability is obtained.

EXAMPLE 7 (GRANULE)

1 part of polyacrylamide is added to 99 parts of powdery calcium carbonate, and a suitable amount of water is added to the mixture and it is kneaded. The kneaded mixture is granulated by a granulator of the screw extruder type, following which the granulated mixture is dried and the size is adjusted to obtain a granular carrier having a size of 12 - 48 mesh. 95 parts of the so obtained carrier is charged in a Nauta mixer, and 5 parts of Formothion liquid (organic solvent dilution of an active ingredient concentration of 80%) is added under agitation to the carrier to make the liquid absorbed in the carrier. Then, 5 parts of granular anhydrous calcium chloride having the size adjusted to 12 – 48 mesh is added to the chemical-absorbed carrier, and the mixture is blended under agitation to disperse calcium chloride uniformly and obtain a granule.

EXAMPLE 8 (MIXED WETTABLE POWDER)

A ribbon-type mixer is charged with 20 parts of Benomyl wettable powder (50%, manufactured by E. I. Du Pont de Nemours & Co., U.S.A.), 50 parts of Difoltan (N-1,1,2,2-tetrachloroethylmercapto-4-cyclohexene-1,2-dicarboximide), 2 parts of white carbon, 3 parts of Sorpol 2495-G (an anionic surface active ingredient, manufactured by Toho Kogaku Kogyo K. K., Japan), 7 parts of anhydrous calcium chloride and 14 parts of clay under agitation. The resulting mixture is pulverized by a hammer mill to obtain a wettable powder.

The effects of the stable agricultural chemical composition of this invention will now be illustrated by reference to the following Tests.

TEST 1 (HIGH TEMPERATURE AND HIGH HUMIDITY ACCELERATED TEST)

Thiadiazine was formed into preparations according to the methods described in Example 1 (powder), Example 3 (wettable powder) and Example 6 (fine granule F), and Dimex was formed into preparations according to the methods described in Example 2 (powder) and Example 5 (wettable powder). Aramite and C-940 were formed into preparations according to the method described in Example 4 (wettable powder), and Formothion was formed into preparations according to the method described in Example 7 (granule). Each wettable powder was packaged in an aluminum foil bag and each of powders, fine granules F and granules was packaged in an aluminum-laminated kraft bag. Each sample was stored for 8 weeks under high temperature and high humidity conditions of a temperature of 40° C and a relative humidity of 80%, and the content of the active ingredient was determined and the residual ratio of the active ingredient after 8 weeks' storage was calculated to obtain results shown in Table 1. The difference of the amount of calcium chloride incorporated was compensated by adjustment of the amount of the inert carrier. In the case of a wettable powder of Zineb, the product was taken out of a bag and was mixed with a prescribed amount of anhydrous calcium chloride, and the mixture was blended, pulverized and tested. It is known that decomposition of Zineb is accelerated once the bag of the product is opened. As is apparent from the results shown in Table 1, in each of the active ingredients, a prominent stabilizing effect was obtained by incorporation of calcium chloride. In the case of Thiadiazine, tendency of caking was extreme in the non-calcium chloride-added control, but this undesired tendency was highly improved by addition of calcium chloride and this tendency was not observed at all when 3% of calcium chloride was incorporated.

Table 1

| Active Ingredient | Preparaion Form | Amount Added(%) of Anhydrous Calcium Chloride | Active Ingredient Residual Ratio (%) |
|---|---|---|---|
| Thiadiazine | powder | 0 | 73.0 |
|  |  | 1 | 87.0 |
|  |  | 3 | 92.7 |
|  |  | 5 | 94.3 |
| Thiadiazine | wettable powder | 0 | 75.6 |

Table 1-continued

| Active Ingredient | Preparaion Form | Amount Added(%) of Anhydrous Calcium Chloride | Active Ingredient Residual Ratio (%) |
|---|---|---|---|
|  |  | 1 | 89.9 |
|  |  | 3 | 92.8 |
|  |  | 5 | 95.0 |
| Thiadiazine | fine granule F | 0 | 71.2 |
|  |  | 1 | 86.0 |
|  |  | 3 | 90.2 |
|  |  | 5 | 92.9 |
| Zineb | wettable powder | 0 | 77.3 |
|  |  | 1 | 91.2 |
|  |  | 3 | 95.0 |
|  |  | 5 | 95.9 |
| Dimex | powder | 0 | 26.5 |
|  |  | 1 | 63.7 |
|  |  | 3 | 80.2 |
|  |  | 5 | 88.9 |
| Dimex | wettable powder | 0 | 43.6 |
|  |  | 1 | 70.2 |
|  |  | 3 | 87.5 |
|  |  | 5 | 90.3 |
| Aramite | wettable powder | 0 | 55.7 |
|  |  | 1 | 83.2 |
|  |  | 3 | 92.3 |
|  |  | 5 | 93.8 |
| C-940 | wettable powder | 0 | 43.0 |
|  |  | 1 | 75.2 |
|  |  | 3 | 90.1 |
|  |  | 5 | 92.8 |
| Formothion | granule | 0 | 21.8 |
|  |  | 1 | 82.5 |
|  |  | 3 | 89.7 |
|  |  | 5 | 91.0 |

Test 2

According to the method described in Example 3, a Thiadiazine wettable powder in which 1, 3, 5 or 10% of anhydrous calcium chloride, calcium chloride dihydrate or calcium chloride hexahydrate (control) was incorporated, was prepared, and the resulting sample was subjected to the accelerated test in the same manner as in Test 1 and the main ingredient residual ratio was determined to obtain results shown in Table 2.

Table 2

| Stabilizer | Amount Incorporated | | | |
|---|---|---|---|---|
|  | 1% | 3% | 5% | 10% |
| Anhydrous | 87.0% | 92.7% | 94.3% | 95.2% |
| Dihydrate | 80.1% | 89.3% | 93.8% | 95.1% |
| Hexahydrate | 71.7% | 70.5% | 70.4% | 67.7% |

From the results shown in Table 2, it is seen that the dihydrate exhibits a similar stabilizing effect if the amount incorporated is a little increased as compared with the case of the anhydride. In contrast, the hexahydrate has no substantial effect.

Test 3 (Effect Test After Accelerated Test)

A Thiadiazine wettable powder containing 5% of anhydrous calcium chloride was prepared according to the method described in Example 3. This wettable powder and a comparative Thiadiazine wettable powder free of calcium chloride were stored under conditions of a temperature of 40° C and a relative humidity of 80% for 8 weeks and their effects were tested.

Seedlings of tomato (variety: Skinfukuju) were cultivated in pots of 9 cm diameter at a density of one seedling per pot, and when 5 to 6 leaves were developed, an aqueous suspension formed by diluting the wettable powder 800 or 1600 times with water was sprayed so that the suspension flowed down in drops from the tomato plant.

The suspension-sprayed plants were air-dried, and then, a suspension of spores of Phytophthora infestans was sprayed and the tomato plants were infected with the pathogenic bacterium. Then, the plants were allowed to stand still for 5 days in a chamber maintained at 20° C to thereby cause the disease in the plants. With respect to all the leaves, the affected area was determined. The test was conducted by the one section-three line system. The test results are shown in Table 3.

Table 3

|  | Ratio (%) of Affected Area to Total Leaf Area | |
| --- | --- | --- |
|  | Active Ingredient Concentration of 1000 ppm | Active Ingredient Concentration of 500 ppm |
| 5% Calcium Chloride-Incorporated Thiadiazine | 0 | 7 |
| Calcium Chloride-Free Thiadiazine (Comparison) | 10 | 28 |
| Non-Chemical-Applied Control | 100 | |

Test 4 (Phytotoxicity Test)

Tomato seedlings used in Test 3 were allowed to stand still for 1 week as they were, and it was examined whether phytotoxicity was caused or not on the tomato seedlings to obtain results shown in Table 4.

Table 4

|  | Degree of Phytotoxicity | |
| --- | --- | --- |
|  | Active Ingredient Concentration of 1000 ppm | Active Ingredient Concentration of 500 ppm |
| Calcium Chloride-Incorporated Thiadiazine | — | — |
| Calcium Chloride-Free Thiadiazine (Comparison) | — | — |
| Non-Chemical-Applied Control | — | |

Notes: — : no phytotoxicity was observed
+ : slight phytotoxicity was observed

Test 5 (High Temperature and High Humidity Accelerated Test)

The Benomyl-Difoltan mixed wettable powder described in Example 8 and the wettable powder containing no anhydrous calcium chloride and prepared according to Example 8 were packaged in aluminum-laminated kraft bags, respectively. Each sample was stored for 8 weeks under high temperature and high humidity conditions of a temperature of 40° C and a relative humidity of 80% and the content of one of the active ingredients, Benomyl was determined and the residual ratio of the Benomyl was calculated to obtain the results shown in Table 5.

Table 5

| Stabilizer Amount (%) | Residual Ratio of Benomyl (%) |
| --- | --- |
| 0 | 63.0 |

Table 5-continued

| Stabilizer Amount (%) | Residual Ratio of Benomyl (%) |
| --- | --- |
| 7 | 95.2 |

As is apparent from the results in Table 5, the wettable powder of Benomyl and Difoltan according to this invention is highly stabilized, while the control wettable powder containing no stabilizer is extremely unstable due to easy degradation of Benomyl in a mixed wettable powder.

What is claimed is:

1. A stable solid agricultural chemical composition comprising an unstable agricultural chemical active ingredient is an agriculturally effective amount selected from the group consisting of 3,3'-ethylenebis (tetrahydro-4,6-dimethyl-2H-1,3,5-thiadiazine-2-thione), zinc ethylenebisdithiocarbamate, manganese ethylenebisdithiocarbamate, methyl 1-(butylcarbamoyl)-2-benzimidazole carbamate, O,O-dimethyl-S-(N-methyl-N-formyl-carbamoylmethyl) phosphorodithioate, O,O-dimethyl-S-2-(ethylthio)ethyl phosphorodithioate, O,O-dimethyl O-(5-phenyl-3-isoxazolyl)phosphorothioate, 2-(p-tert-butylphenoxy)-isopropyl-2'-chloroethyl sulfite, 2-(p-tert-butylphenoxy)-1-ethyl-O-tolyl sulfite and cycloheximide, and a stabilizer selected from the group consisting of anhydrous calcium chloride, calcium chloride monohydrate, calcium chloride dihydrate and mixtures thereof, said stabilizer being present in an amount effective to stabilize the composition against deterioration due to elevated temperature and high humidity conditions.

2. A stable solid agricultural chemical composition as set forth in claim 1 wherein the calcium chloride stabilizer is incorporated in an amount of 0.1 to 20% by weight based on the composition.

3. A stable solid agricultural chemical composition as set forth in claim 2 wherein the calcium chloride stabilizer is incorporated in an amount of 3 to 10% by weight based on the composition.

4. A process for the preparation of a stable solid agricultural chemical composition which comprises mixing with an agriculturally effective amount of an unstable agricultural chemical selected from the group consisting of 3,3'-ethylenebis(tetrahydro-4,6-dimethyl-2H-1,3,5-thiadiazine-2-thione), zinc ethylenebisdithiocarbamate, manganese ethylenebisdithiocarbamate, methyl 1-(butylcarbamoyl)-2-benzimidazole carbamate, O,O-dimethyl-S-(N-methyl-N-formylcarbamoylmethyl) phosphorodithioate, O,O-dimethyl-S-2-(ethylthio)ethyl phosphorodithioate, O,O-dimethyl-O-(5-phenyl-3-isoxazolyl)phosphorothioate, 2-(p-tert-butylphenoxy)isopropyl-2'-chloroethyl sulfite, 2-(p-tert-butylphenoxy)-1-ethyl-O-tolyl sulfite and cycloheximide, a stabilizer selected from the group consisting of anhydrous calcium chloride, calcium chloride monohydrate, calcium chloride dihydrate, and combinations thereof, the amount of said stabilizer being effective to stabilize the unstable agricultural chemical against deterioration due to high humidity and elevated temperature.

* * * * *